US00RE35227E

United States Patent [19]

Tomioka et al.

[11] E Patent Number: Re. 35,227

[45] Reissued Date of Patent: May 7, 1996

[54] PROCESS AND APPARATUS FOR ANALYZING CELLS

[75] Inventors: Atuo Tomioka; Masayuki Nakagawa, both of Hyogoken; Tadashi Maeda, Kobe, all of Japan

[73] Assignee: Toa Medical Electronics Co., Ltd., Kobe, Japan

[21] Appl. No.: 198,461

[22] Filed: Feb. 17, 1994

Related U.S. Patent Documents

Reissue of:

[64] Patent No.: 5,088,816
Issued: Feb. 18, 1992
Appl. No.: 489,463
Filed: Mar. 6, 1990

[30] Foreign Application Priority Data

Sep. 19, 1989 [JP] Japan ..... 1-243107

[51] Int. Cl.[6] ..... G01N 21/05

[52] U.S. Cl. ..... 356/39; 356/246

[58] Field of Search ..... 356/39, 246; 382/133

[56] References Cited

U.S. PATENT DOCUMENTS 4,338,024 7/1982 Bolz et al. ..... 356/39
4,519,087 5/1985 Deindoerfer ..... 356/39

FOREIGN PATENT DOCUMENTS 57-500995 6/1982 Japan .

*Primary Examiner*—Richard A. Rosenberger
*Attorney, Agent, or Firm*—Peter Jon Gluck; Thomas R. Morrison

[57] ABSTRACT

A cell analyzing system flows a liquid to be tested and a sheath liquid through a flattened flow passage. An image of the flattened flow passage is formed at two different magnifications. The thickness of the liquid to be tested in the flattened flow passage is changed between the two different magnifications to maintain this thickness at a value smaller than a depth of field of the apparatus forming the image. The thickness of the liquid to be tested is changed by changing its flow relationship to the sheath liquid.

16 Claims, 8 Drawing Sheets

PROCESS AND APPARATUS FOR ANALYZING CELLS

Matter enclosed in heavy brackets [ ] appears in the original patent but forms no part of this reissue specification; matter printed in italics indicates the additions made by reissue.

BACKGROUND OF THE INVENTION

This invention relates to apparatus and processes for analyzing a liquid to be tested such as, for example, a urine sample collected from a living body. The liquid flows in a flattened sheet, surrounded by a sheath liquid. The orientations of respective ingredients in the liquid to be tested are placed in a condition that permits the classification and counting of the ingredients through image processing. More specifically, during the measurement, the classification and counting are carried out by changing the magnification of the optical system.

Microscopic examination of urine sedimentation is a well-known clinical examination technique that continues in common use. This examination requires only a very simple collection of urine from a patient. An examination of sedimentation in the urine, can help determine the conditions of kidneys, urinary and genital organs, since urine contains red blood corpuscles from capillary vessel bleeding, white blood corpuscles from the vessel, epithelium of kidney or urinary/genital organs, columnal kidney tubules and microorganisms associated with infection.

In a conventional examination, components in the urine are separated in a centrifuge. The sediment is placed on a microscope slide to make a sample. Then, the ingredients of the sample are examined and classified by microscopic observation.

Conventional examination suffers from the disadvantage that some ingredients of the urine are damaged during centrifugal separation. The accuracy of determining the concentration of a component is complicated by the process of centrifugal separation. Further, microscopic observation needs a very precise classification of respective ingredients, and the number of the ingredients to be observed is small. In addition, the ingredients are scattered irregularly within the sample. This makes the process very burdensome for examining technicians. As a result, conventional examination may produce errors in the analysis of the urine.

A more accurate and less labor-intensive technique employs an automatic urine analyzing device. A liquid to be tested, surrounded by an outer layer of a sheath liquid, is transformed into a very flattened flowing sheet of liquid. The flattened sheet of liquid is photographed by a video camera. The resulting static image is analyzed by image processing techniques to classify and count the ingredients in the liquid to be tested.

Microscopic examination of such a flattened sheath flow method must meet the following two (2) requirements:

(1) Flattened ingredients such as red blood corpuscles must be oriented in a certain direction. This aims at obtaining the image of the ingredients.

(2) The liquid to be tested must be transformed into a flattened flow liquid. The thickness of the flattened flow liquid is less than the depth of field of the video camera. This produces a very well-focused image. Also, by flattening the liquid to be tested, the particles to be detected are spread widely across the photographic image.

Examples of the foregoing flattened sheath flow method are disclosed in Japanese Patent Publication 57-500995 and U.S. Pat. No. 4,338,024. In order to photograph the static image of the ingredients in the flattened sheath flow, a strobe light having a short emitting time or a pulse laser light is irradiated through the thin cross section of the flattened flow. The image is photographed through the objective lens of a video camera.

The kinds and sizes of ingredients in a urine sample vary. For example, the diameter of a red blood corpuscle is about 10 micrometers. The diameter of the epithelium is a little larger, i.e., several tens of micrometers. In some cases, a columnal tubule is from several hundred micrometers to 1 or 2 millimeters in length. It is impossible to photograph and analyze respective ingredients having such a range of sizes at the same magnification.

Therefore, the magnification must be changed during a measurement process. Smaller ingredients are photographed at a high magnification, and larger ingredients are photographed at low magnification.

However, when the magnification of the lens is changed, the depth of field of the lens is also changed. At high magnification, the depth of field is reduced. In the flat-sheath flow method, if the flattened stream is thin enough, focusing can be accomplished at both high and low magnification. However, using the same thickness for both magnifications has a drawback. At low magnification, a stream that is thin enough to maintain focus at high magnification, is too thin to contain enough of the larger particles that are the target at such low magnification. The small number of particles degrades measurement accuracy.

OBJECTS AND SUMMARY OF THE INVENTION

It is therefore a general object of the invention to provide a cell analyzing process and apparatus in which a liquid to be tested flows in a thin sheet past a lens of high magnification, and in a thicker sheet past a lens of low magnification, whereby a clear image is available at either magnification, and sufficient particles are present within the thickness dimension of the sheet to permit effective analysis to be done.

It is a further object of the invention to provide a cell analyzing technique having provision for simultaneous control of a magnification, a thickness dimension of a flattened layer of liquid to be tested, and a light intensity.

Briefly stated, the present invention provides a cell analyzing system wherein a liquid to be tested and a sheath liquid flow through a flattened flow passage. An image of the flattened flow passage is formed at two different magnifications. The thickness dimension of the liquid to be tested in the flattened flow passage is changed between the two different magnifications to maintain this thickness dimension at a value smaller than a depth of field of the apparatus forming the image. The thickness dimension of the liquid to be tested is changed by changing its flow relationship to the sheath liquid.

According to an embodiment of the invention, there is provided a process for classifying and counting ingredients of a liquid to be tested, comprising: flowing the liquid to be tested in a flattened path, surrounding the liquid to be tested in the flattened path with a sheath liquid, impinging a light on the flattened path, photographing the flattened path at a first magnification, photographing the flattened path at a second magnification, changing a thickness dimension of the liquid to be tested in the flattened path when photographing at the first and second magnifications, whereby the thickness dimension remains less than a depth of field of a lens used in the photographing.

According to a feature of the invention, there is provided a cell analyzing system comprising: a strobe for emitting flashes of a light, at least one lens, the at least one lens being effective for transforming the light into a parallel light, an iris receiving the parallel light, adjustable means for adjusting an opening of the iris, a condenser lens receiving light from the iris, a flow cell, a reduced flow passage in the flow cell, the reduced flow passage including a thickness dimension which narrows gradually in a downstream direction, a flattened flow passage, the flattened flow passage having a smaller thickness dimension than the reduced flow passage and communicating with a downstream side thereof, a nozzle having an end facing in a downward direction toward an upstream side of the reduced flow passage, a test liquid supply means, the test liquid supply means being connected to the nozzle, the test liquid supply means including means for changing the supply quantity of the liquid to be tested, a sheath liquid supply means connected to an upstream side of the reduced flow passage, at least the flattened flow passage being transparent, the light from the condenser lens passing through the flattened flow passage, including liquids therein, an objective lens disposed behind the flow cell, at least first and second projection lenses, the at least first and second projection lenses having first and second different magnifications, means for selectably disposing the first and second projection lenses in a path of light from the flattened flow path, and means for photographing an image from a selected one of the first and second projection lenses.

According to a further feature of the invention, there is provided a method for photographing a test liquid, comprising: flowing the test liquid through a reduced flow passage, flowing the test liquid from the reduced flow passage through a flattened flow passage, flowing a sheath liquid through the flattened flow passage, passing parallel light through the flattened flow passage, forming an image of the parallel light passing through the flattened flow passage, controlling a thickness dimension of the test liquid in the flattened flow passage to a value permitting the image to be sharp, and the step of controlling including changing a flow relationship of the test liquid and the sheath liquid.

The above, and other objects, features and advantages of the present invention will become apparent from the following description read in conjunction with the accompanying drawings, in which like reference numerals designate the same elements.

DETAILED DESCRIPTION OF PREFERRED EMBODIMENTS

Figure 1:
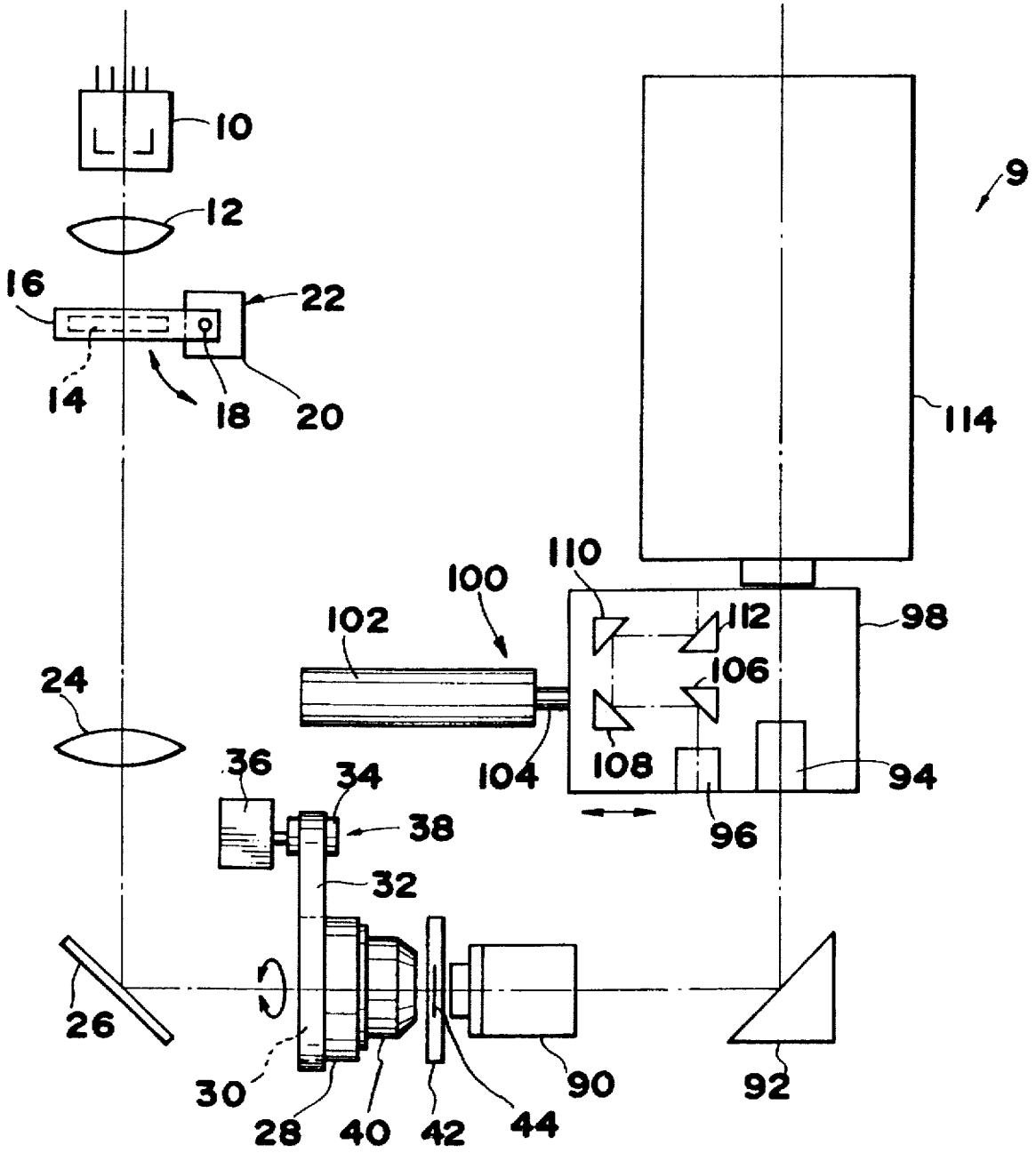
FIG. 1 is a schematic view of the optical components of a cell analyzing apparatus according to this invention.
Figure 2:
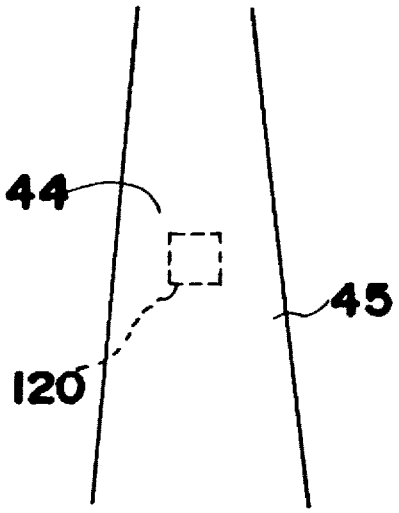
FIG. 2 is a view of an example of a flattened flow passage, including the field of view at high magnification.
Figure 4:
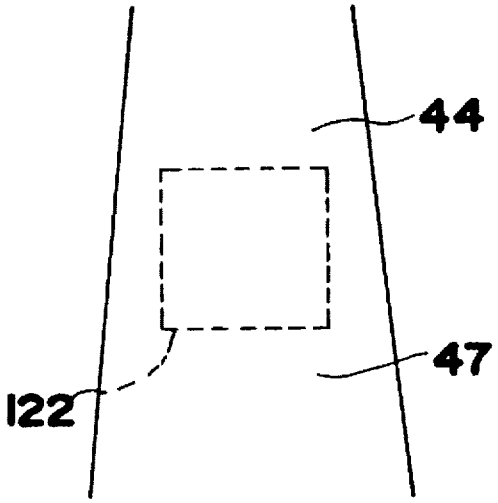
FIG. 4 is a view of an example of a flattened flow passage, including the field of view at low magnification.

Referring to FIG. 1, a cell analyzing apparatus 9 includes an optical axis, indicated in dash-and-dot line. A strobe 10 emits a brief flash of light for about 5 microseconds every 1/30 of a second. The light from the strobe 10 is collected by a collecting lens 12, transformed to parallel light by a field lens 24, reflected about 90 degree by a mirror 26 and is then incident upon an iris 28. A diffusing plate 14 is disposed between the collecting lens 12 and the mirror 26. The diffusing plate 14 is mounted in a retainer 16 which is rotatably supported by a rotatable shaft 18 of a rotary actuator 20. A moving means 22 of rotary actuator 20 rotates diffusing plate 14 is synchronism with the operation of strobe 10, whereby diffusing plate 14 is moved into, and out of, the light from collecting lens 12 during selected flashes of strobe 10. In this way, one light pulse from the strobe 10 passes through the diffusing plate 14, and the next light pulse goes directly to field lens 24, without passing through diffusing plate 14. Conditions may arise requiring that diffusing plate 14 be in an operational position at all time, or not at all.

The light is diffused by passing through the diffusing plate 14, whereby non-uniformity of luminous intensity across the cross section of the light beam is substantially eliminated, and a uniform light is formed.

The opening of iris 28 is adjusted by a movable means 38 to adjust the amount of light passing therethrough. The iris 28 is rotated by a movable means 38 to change the area of its opening.

The movable means 38 comprises a toothed pulley 34 mounted on the shaft of a motor 36. A second toothed pulley 30 is mounted on an outer periphery of the iris 28. A timing belt 32 engages the toothed pulleys 30 and 34.

After passing through the opening of the iris 28, the light is collected by a condenser lens 40, and then impinged on a small area of a flattened flow passage 44 in a flow cell 42. The liquid to be tested flows through flattened flow passage 44.

When the opening of iris 28 is reduced, the quantity of light passing therethrough is reduced, and the depth of field of condenser lens 40 is increased. Increasing the opening of iris 28 increases the light passing therethrough, and [increases] *reduces* the depth of field of condenser lens 40. After passing the flow cell 42, the image thereof is enlarged by an objective lens 90 having a magnification of, for example, 10, reflected by a mirror 92, and then passes through a projection lens 94 or 96, for recording in a photographing means 114 such as a video camera. The magnification of respective projection lenses 94 and 96 is one time and four times.

The projection lenses 94, 96 are retained by a retainer 98 which is reciprocated by a first moving means 100. The first moving means 100 is driven by a piston 104 of an air cylinder 102 attached to the retainer 98. A linear slide (not shown) is preferably provided to constrain the retainer 98 to move in the required linear motion.

When first moving means 100 is in the position that selects the projection lens 94, the total magnification is the same as that provided by objective lens 90 alone, i.e., 10×. The light passes directly from the lens 94 into photographing means 114, wherein an image is formed.

When the first moving means 100 is in its alternate position wherein projection lens 96 is selected, the magnification is increased to 40×. The path length of the light passing through the lens 96 is increased by reflection from a series of mirrors 106, 108, 110 and 112, before it is incident on the photographing means 114. As is conventional, the above-described optical path must be protected from the entry of stray light.

Figure 3:
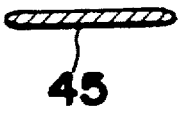
FIG. 3 is a cross section of the flattened test liquid flow in FIG. 2, suitable for use at high magnification.
Figure 5:
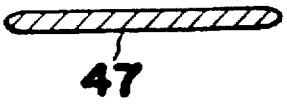
FIG. 5 is a cross section of the flattened test liquid flow in FIG. 4, suitable for use at low magnification.

FIGS. 2 through 5 show liquids to be tested 45, 47 flowing through the flattened flow passage 44 of the flow cell 42. FIGS. 3 and 5 are cross sections of the test liquids 45, 47. The fields of view 120 and 122 at magnifications of 40 and 10, respectively, are indicated in dashed lines in FIGS. 2 and 4. The optical system is designed such that:

0.61 NA/lambda≈2×(pixel dimension)/M at the time of a high magnification.

Wherein:

NA is the number of opening of the lens.

Lambda is a wave-length of light.

M is magnification.

At large magnifications (40×), the depth of field to be photographed is relatively small. For this reason, as shown in FIG. 3, the cross-sectional thickness dimension of the liquid being tested 45 is held to a small dimension in order to keep it to less than the depth of field. Further, in order to photograph possibly many particles, the liquid to be tested must flow in a stream that covers the whole visible area.

At lower magnification (10×), the depth of field is relatively large. Although a thin layer, such as shown in FIG. 3 would permit a sharp focus, the quantity of the liquid contained therein is small. This limits the number of particles available for measurement, thereby decreasing the analytical accuracy. Accordingly, at low magnification, the thickness dimension of the test liquid flow is increased to a value that it a little thinner than the depth of field, as shown in FIG. 5.

As will be explained hereinafter, the thickness dimension of the test liquid flow can be changed by changing the flow of a sheath liquid, changing the flow of the liquid to be tested, or changing the flow of both. It is simpler to keep the flow of the sheath liquid constant and change only the flow of the liquid to be tested.

When transferring from one lens to the other (94 and 96), it is important that the respective lenses be positioned accurately in order to establish the correct focus. The smaller the magnification of the moving lens, the easier it is to attain such accurate positioning. Therefore, the magnification of the lenses to be moved are preferably kept at a low level. In this embodiment, the magnification of the projection lens is 1× and 4×. The remainder of the required magnification is made in the stationary objective lens 90 (10× in the present embodiment). Being stationary, positioning accuracy of the objective lens 90 is easily attained.

Figure 6:
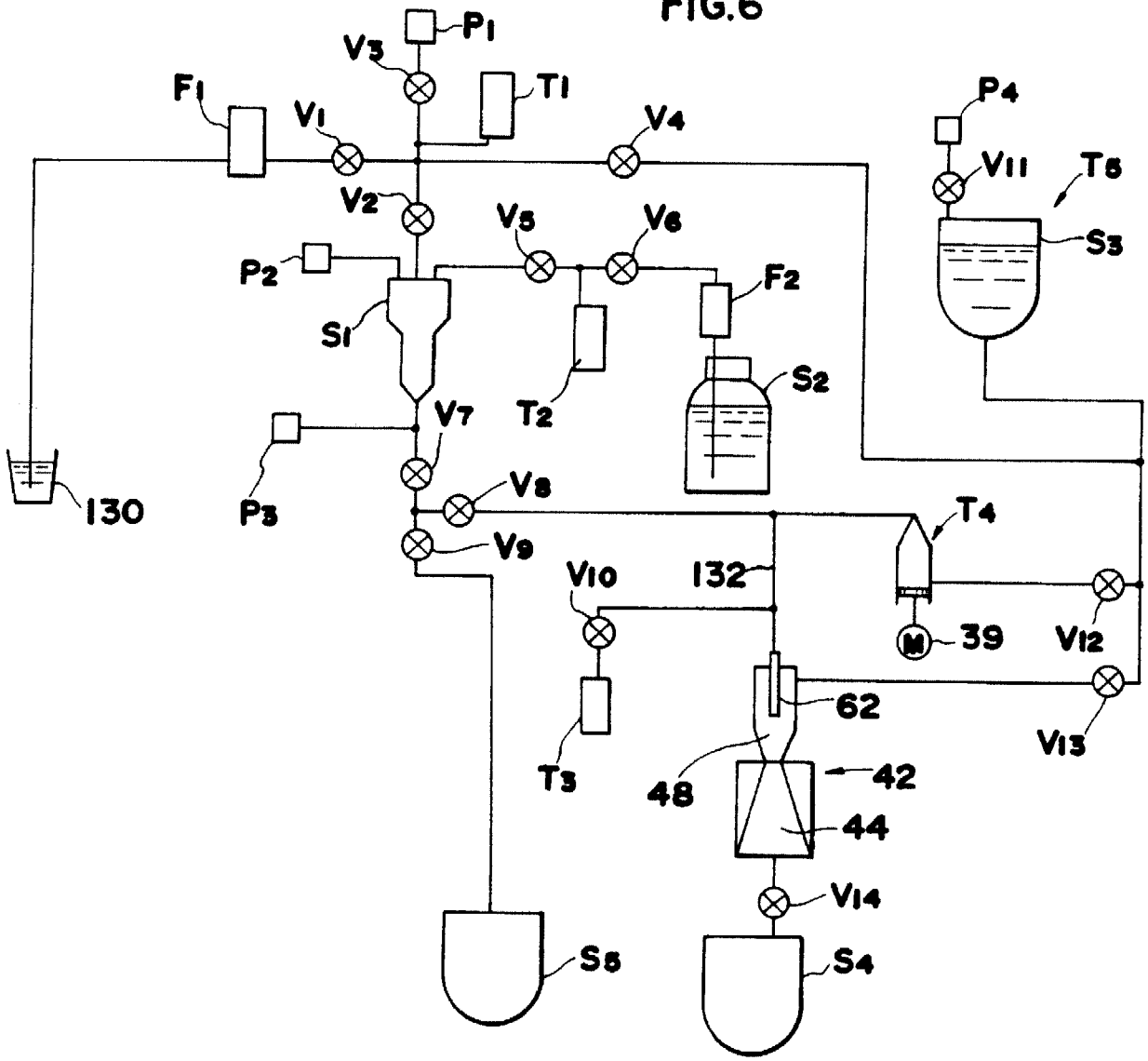
FIG. 6 is a fluid flow circuit diagram of an embodiment of a cell analyzing apparatus according to this invention.
Figure 7:
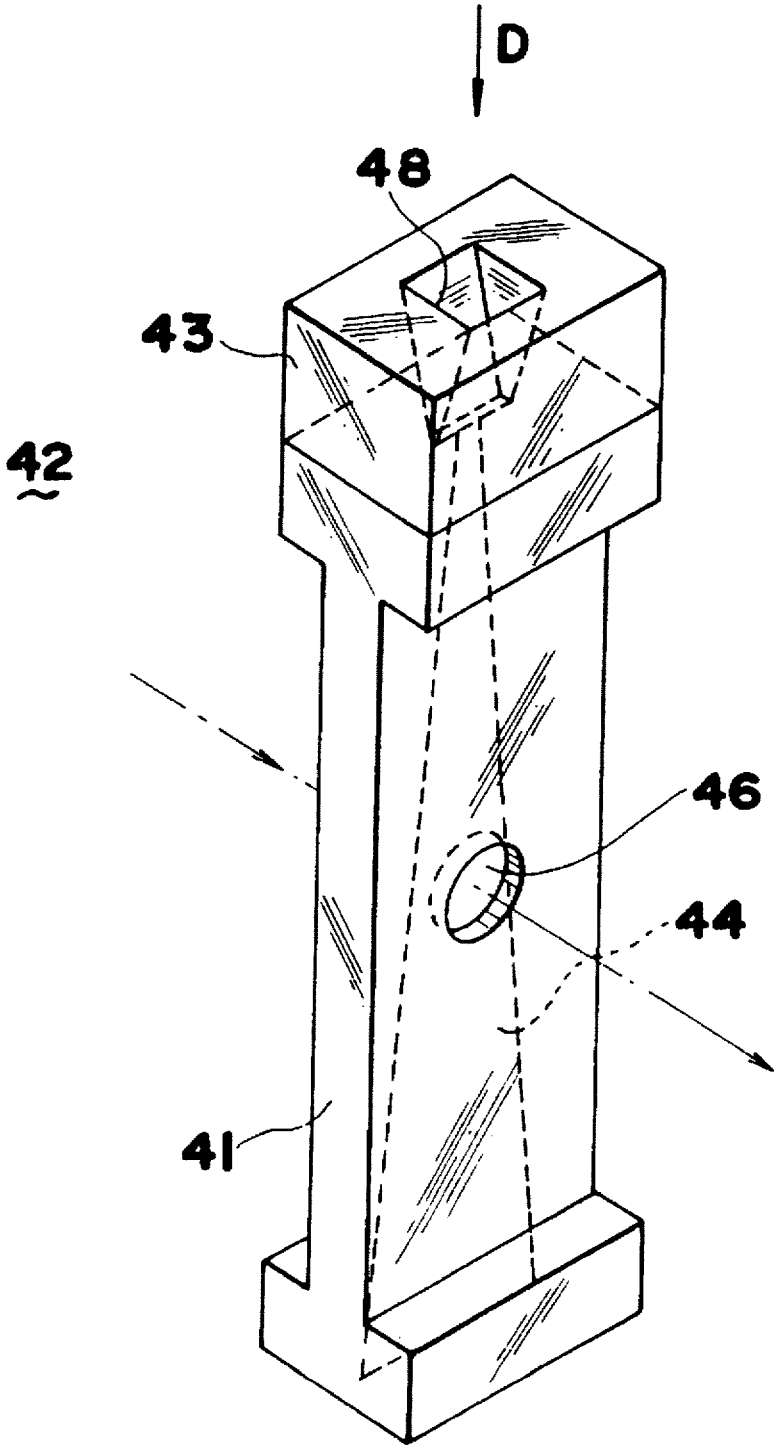
FIG. 7 is a perspective view of the flow cell of FIG. 1.

FIG. 6 shows an embodiment of a fluid circuit diagram of a cell analyzing apparatus according to this invention. First, a valve $V_1$ is opened, and a urine sample 130 to be tested is drawn in by a metering device T1. A filter $F_1$ in the path from urine sample 130 to valve $V_1$ has a pore diameter of at least 250 micrometers. Valve $V_1$ is closed and a valve $V_2$ is opened. A negative pressure sensor $P_2$, connected to a reacting container $S_1$, is actuated to draw the urine sample into the reacting container $S_1$. A predetermined quantity of a dye liquid is drawn into the reacting container $S_1$ by a metering device $T_2$ from a dye liquid container $S_2$ through a filter $F_2$ and a valve V6.

A positive pressure source $P_3$ is actuated intermittently to force bubbles through the urine sample and dyeing liquid in the reacting container $S_1$. The bubbles agitate and mix the liquids in the reacting container $S_1$. After a 45-second dye treatment in reacting container $S_1$, the mixture is drawn through a tube 132 and opened valves $V_7$, $V_8$ and $V_{10}$ by suction of a metering device $T_3$. Any residual liquid in the reacting container $S_1$ is discharged into a waste liquid container S5 by way of valve $V_9$.

Then, a urine sample supply means $T_4$ for supplying the urine sample is placed in its discharge position. The urine sample in the tube 132 is discharged at a constant speed through a nozzle 62 into the flow cell 42. The urine sample supply means $T_4$ is, e.g., a cylinder for supplying the urine sample quantitatively by movement of a piston therewithin. The movement of the piston is controlled accurately by a stepping motor 39. Preferably, the piston is controlled by converting rotation of the motor 39 into linear movement of the piston in urine sample supply means $T_4$.

A sheath liquid supply means $T_5$ comprises a positive pressure source $P_4$ and a sheath liquid container $S_3$. A valve $V_{13}$ permits sheath liquid to flow, under urging from positive pressure source $P_4$, from sheath liquid supply means $T_5$ into reduced flow passage 48. The temperature of the sheath liquid is preferably maintained at a constant value so that a constant pressure from positive pressure source $P_4$ is effective to produce a constant flow of sheath liquid. The foregoing assumes that the pressure supplied by positive pressure source $P_4$ remains constant during delivery.

When the piston of urine sample supply means $T_4$ ascends, the urine sample is discharged through nozzle 62 into reduced flow passage 48 where it flows, surrounded by the sheath liquid. The flow of the urine can be changed by changing the rotation speed of the motor 39. Since the sheath liquid is supplied at a constant flow, the ratio of the sheath liquid to the urine sample to be tested can be changed by changing the flow of the urine sample. This also changes the thickness dimension of the liquid to be tested.

In operation valves $V_{11}$ and $V_{13}$ are opened to permit the flow of the sheath liquid from the sheath liquid container $S_3$ under urging by the pressure in positive pressure source $P_4$. A valve $V_{14}$ is opened to permit discharge of the liquid to be tested and the sheath liquid flowing from the flattened flow passage 44 of the flow cell 42 into the waste liquid container $S_4$.

The liquid to be tested flowing in the flattened flow passage 44 is photographed by a suitable optical system, and subsequently the image of respective ingredients in the urine sample can be extracted by means of image processing. If sufficient dyeing time is not available because of the number of samples to be tested, first, all the particles adaptable to easy dyeing are photographed and then the other particles not adaptable to easy dyeing are done. During subsequent processing, the sheath liquid is supplied into the flow passages from the valves $V_4$, $V_{12}$, and $V_{13}$.

The input line and filter $F_1$ are purged by opening the valves $V_3$ and $V_1$ and permitting compressed air from the positive pressure source $P_1$ to expel the liquid back into the urine sample 130.

Referring now to FIGS. 7,8,9 and 10, a dot-dash line in flow cell 42 indicates an optical axis. The flow-cell 42 comprises a first cell 41 and a second cell 43, with which the flattened flow passage 44 of the first cell 41 is integrally communicated with a reduced flow passage 48 of the second cell 43. The first cell 41 and the second cell 43 are bonded together using, for example, an ultraviolet hardening adhesive. Further, they are made of a plurality of glass members.

Figure 11:
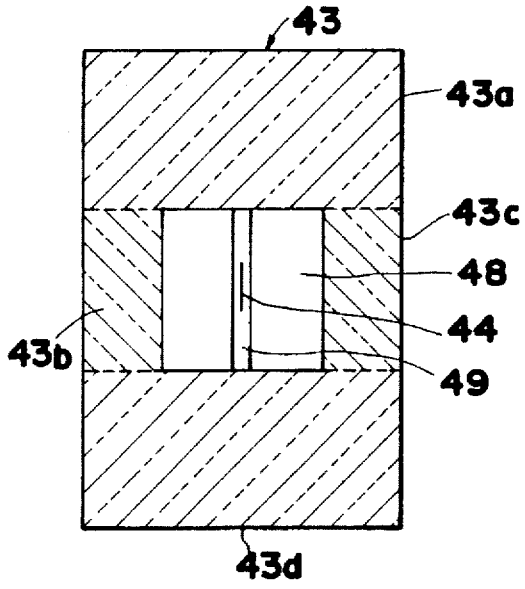
FIG. 11 is an expanded cross section seen from the direction D in FIG. 7.

Referring to FIG. 11, the second cell 43 consists of glass members 43b, 43c in which one side of a rectangular body is cut off obliquely, as well as of glass members 43a, 43d of the rectangular body. The two surfaces of the obliquely cut-off glass members 43b, 43c are opposed to each other. A gap is disposed at the bottom of the two oblique surfaces. The glass members 43b, 43c are supported by the glass members 43a, 43d. Those members 43a, 43b, 43c and 43d are integrally joined together by, for example, melting.

The reduced flow passage 48 having a square top opening is formed inside the second cell 43. The reduced flow passage 48 converges in the direction of the optical axial.

Figure 10:
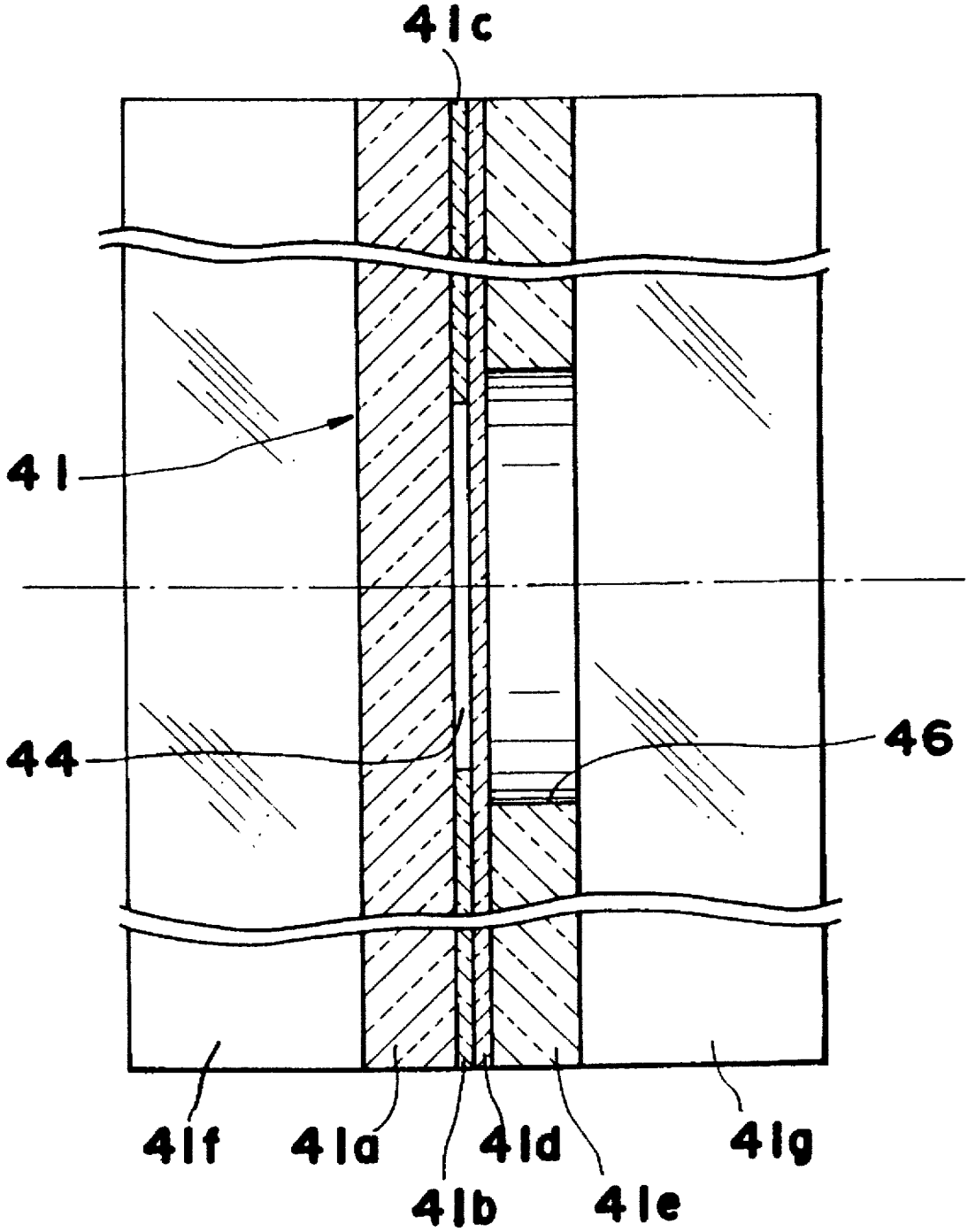
FIG. 10 is an enlarged cross section taken on line B—B in FIG. 8 (or taken on line C—C in FIG. 9).

As shown in FIG. 10, the first cell 41 consists of plate-shaped glass members 41a, 41b, 41c, 41d and 41e, all of which are joined by any convenient means such as, for example, by melting. More specifically, the thickness of the glass member 41a at the side of a light source is relatively thick, i.e., 1 mm. Disposed on the rear surface of the glass member 41a (at the photographing side) are two glass members 41b, 41c having a relatively thin thickness, i.e., several hundred micrometers, forming a gap therebetween. As clearly illustrated in FIGS. 7 and 8, the gap is narrow, i.e., about 1 mm at its uppermost end, but diverging gradually in a downward direction to a width of, for example, about 10 mm. A thin glass member 41d is disposed on the rear side between the glass members 41b, 41c to fill the gap.

The glass member 41d has nearly same the thickness (0.17 to 0.18 mm) as a conventional cover glass for a microscope slide. Supporting the glass members 41b and 41c by the glass members 41a, 41d, the gap is the entry into the flattened flow passage 44.

Since the outer wall of the glass member 41d at the photographing side is very thin, the objective lens can approach very close to the liquid being tested, flowing in the flattened flow passage. If this thickness were greater, the distance from the objective lens to an object to be photographed would be great enough to prevent a sharp focus.

When the test liquid flowing in the flattened flow passage 44 is a urine sample, it may contain particles including red blood corpuscles, epithelium, columnar tubules and the like. Further, when the thickness of the glass over the object to be photographed is about 0.17 mm or 0.18 mm as discussed above, the objective lens is capable of approaching close enough to obtain a sharp focus. If the glass were thicker, this would not be possible.

However, when the rear-glass of the first cell 41 is thin, even a small amount of pressure may break it. Therefore, reinforcement is necesssary. In this embodiment, the plate-shaped glass member 41e, having the nearly same thickness (1 mm) as the glass member 41a, is joined to the latter to provide reinforcement. Further, in order that the first cell 41 and the second cell 43 may be joined easily together and the flow cell 42 may be retained easily by other members, the front and rear surfaces of the first cell 41 are bonded to the rectangular glass members 41f, 41g, 41h and 41i, preferably using an infrared hardening-type adhesive or the like. Alternatively, it is possible to insert a thin packing between the first cell 41 and the second cell 43 under application of upward and downward pressure.

As discussed above, the flow cell 42 is produced in combination with a plurality of simply shaped glass members, so that it is relatively easy to produce even a flow cell having a complicated shape.

As shown in FIG. 11, the reduced flow passage 48 of the second cell 43 is, at its lower end, provided with the gap 49 having longer and shorter sides that are exactly aligned with those of the flattened flow passage of the first cell 41.

Figure 8:
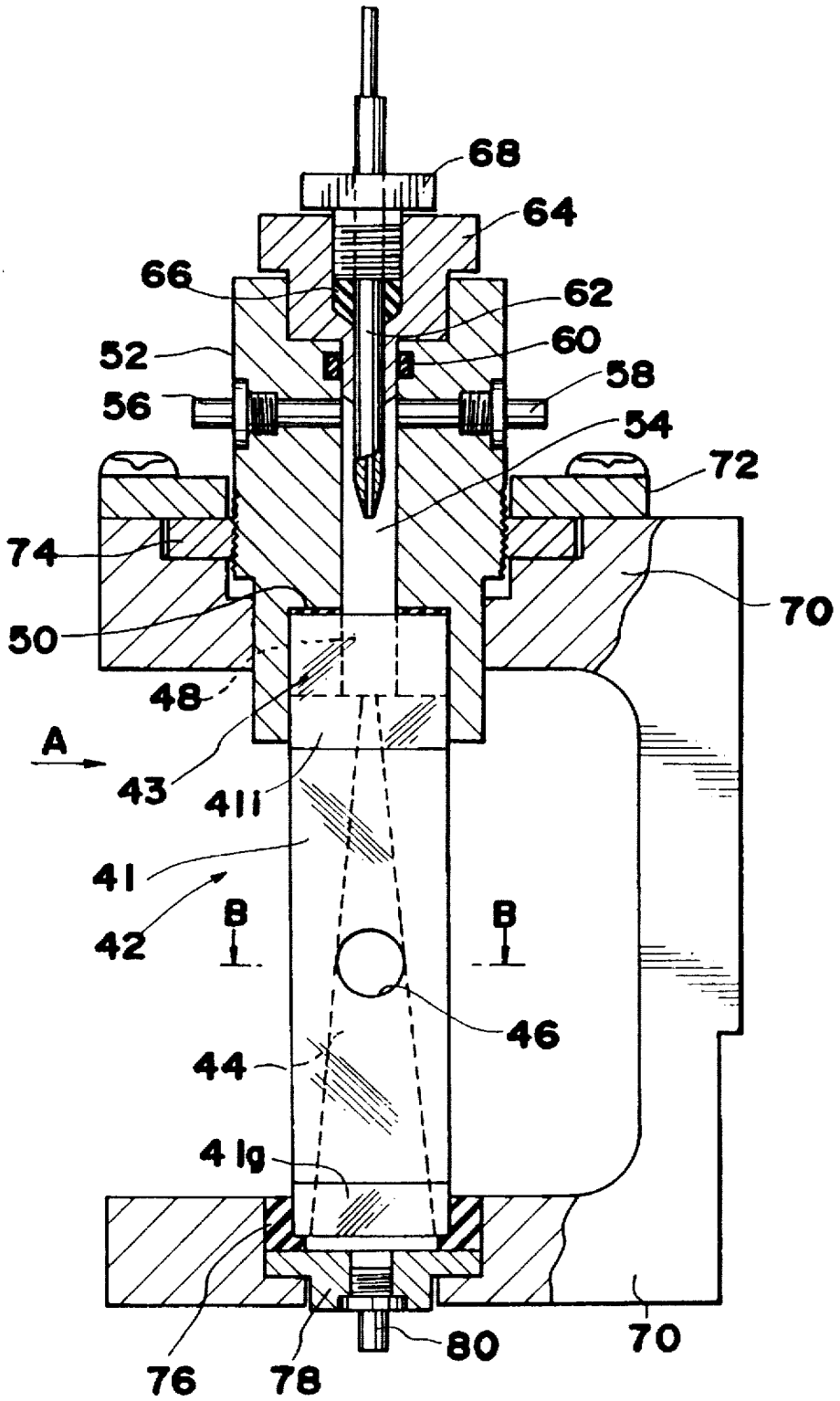
FIG. 8 is a front view, partly in cross section, of the flow cell of FIG. 7.
Figure 9:
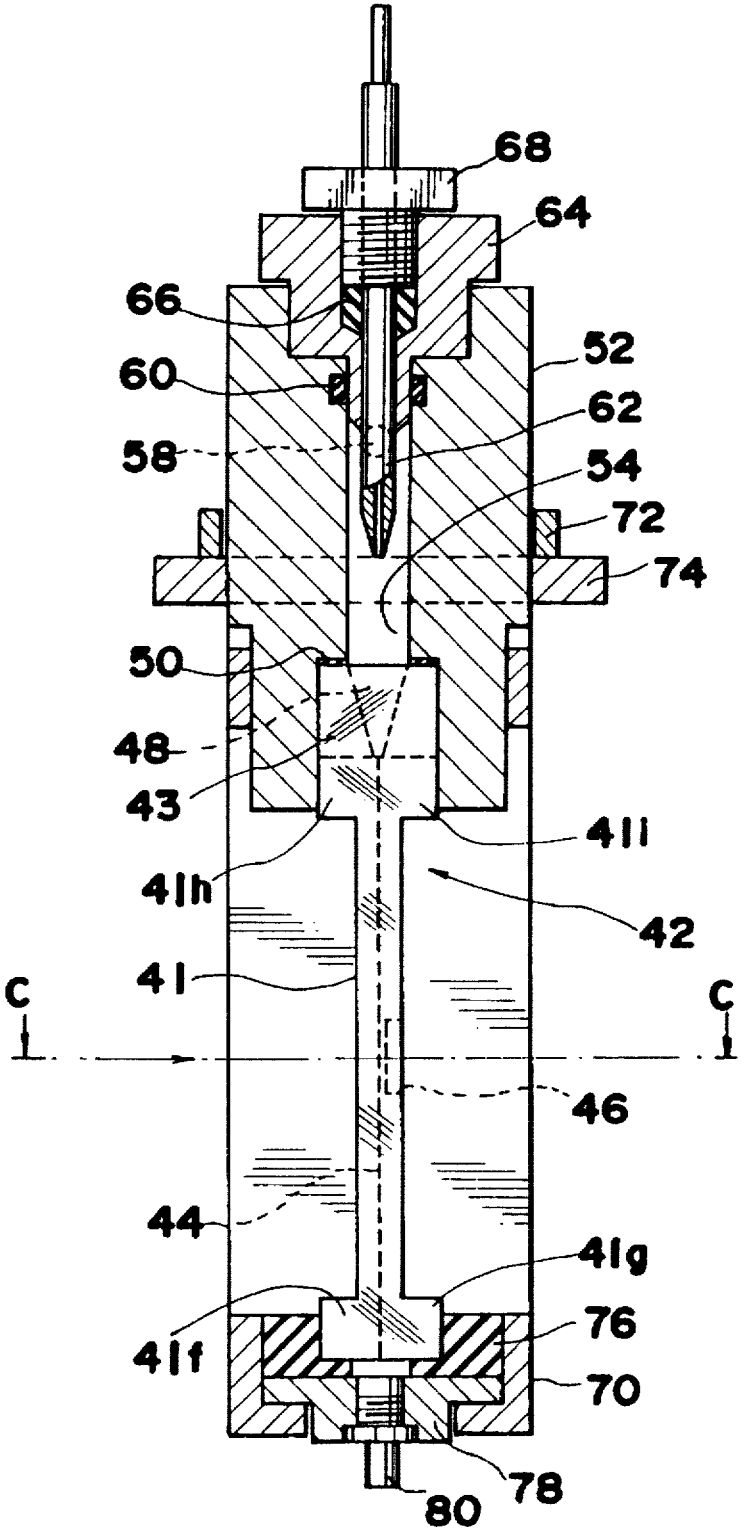
FIG. 9 is a view, partly in cross section, of the left side of the flow cell in FIG. 7.

As shown in FIGS. 8 and 9, the top of the flow cell 42 is, by way of a packing 50, connected to a sheath forming member 52 having nozzle 62 therein. The nozzle 62 is inserted in a retainer 64, and screwed by a fixing tool 68 so as to press on the packing 66. Numeral 60 is an O-ring. The retainer 64, retaining the nozzle 62 therein, is attached to the sheath forming member 52, and the nozzle 62 is disposed in a passage 48 of the flow cell 42. Two nipples 56, 58 permit injection of the sheath forming liquid.

The flow cell 42 and the sheath-forming member 52 are sealed to each other by the packing 50, and retained by a U-shaped flow cell retainer 70. The lower side of the flow cell retainer 70 includes an L-shaped recess, in which are incorporated a retainer 78 having a nipple 80, and a packing 76, upon which is mounted the flow cell 42. The sheath forming member 52, inserted into a recess of an upper side of the flow cell retainer 70, is mounted on the flow cell 42 by way of the packing 50.

A ring-shaped screw 74 includes a screw thread to be engaged with a screw thread formed on an outer surface of the sheath-forming member 52. The ring-shaped screw 74 is rotatably supported upon the flow cell retainer 70 by a plate 72. By rotating the ring-shaped screw 74, the sheath-forming member 52 is moved downwardly relative to the flow cell retainer 70, thereby both the sheath-forming member 52 and the flow cell 42 can be retained between the upper side of and the lower side of the retainer 70.

The urine sample (liquid to be tested), dyed for a certain time by a dying liquid, is extruded at a constant velocity from the nozzle 62. The sheath liquid is supplied at a constant pressure through one or both of the nipples 56 and 58. The liquid to be tested flows surrounded by the sheath liquid in the passage 54. Gradually, the test liquid flow is reduced in the passage 54. However, the flow directions of respective ingredients in the liquid to be tested are not always the same. Some of them could flow meanderingly.

Subsequently, the liquid to be tested, surrounded by the sheath liquid as an outer layer, flows into the reduced passage 48 of the flow cell. The reduced passage 48 is wedge shaped. Although its width narrows greatly in a direction parallel to the optical axis, it remains constant in a direction at right angles to the optical axis. For this reason, the liquid flowing in the wedge-shape reduced passage 48, causes a larger force in a direction (reduced ratio is larger) parallel to the optical axis, but a smaller force in a direction (reduced ratio is smaller) at right angles to the optical axis. Accordingly, the liquid to be tested in a central part of the reduced flow passage 48 flows narrowly in a direction parallel to the optical axis, but widely and flatly in a direction at right angles to the optical axis.

Figure 12:
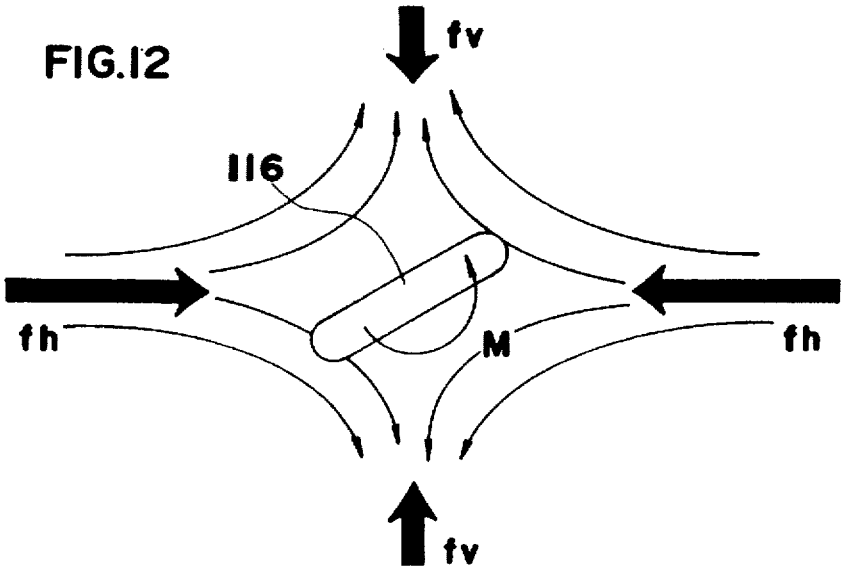
FIG. 12 is a schematic view of force distribution, in which certain forces are imposed on the flattened particles.

As shown in FIG. 12, a flattened particle 116 in the liquid to be tested is subject to a larger force fh and a smaller force fv, whereby a rotary movement M is imposed upon it so as to direct its flattened surface toward the optical axis, and the flattened particle 116 is finally directed to the optical axis.

Subsequently, the liquid to be tested, flattened to some extent by orientation of the test liquid, flows into the flattened flow passage 44 of the flow cell 42. The flattened flow passage 44 is narrower in a direction parallel to the optical axis, and wider in a direction at right angles to the optical axis. As the liquid flows downstream, the thickness of the flattened flow passage 44 becomes narrower in a direction parallel to the optical axis, but wider in a direction at right angles to the optical axis. Since the ratio of width/thickness becomes greater, the liquid flow is gradually flattened, thereby the orientation of respective ingredients are adjusted. The liquid to be tested and sheath liquid flowing in the flattened flow passage 44 are discharged through the nipple 80.

Figure 13:
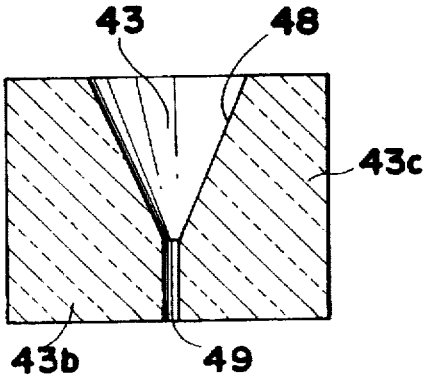
FIG. 13 is a section view of an embodiment of a reduced flow passage.

As shown in FIG. 13, the reduced flow passage 48 of the second cell 43 is reduced and then forms the flattened gap 49. Due to this structure, the liquid flow is flattened till it flows in the flattened flow passage 44.

As described above, the light quantity on the flow cell, the thickness of the test liquid flow and the magnification of the lenses are changed simultaneously so that a clear image, containing plenty of particles, is obtained at all values of magnification.

Under low magnification, the light from the strobe is diffused uniformly by a diffusing plate, so that the intensity across the field of view is uniform. Therefore, a clear image, having a uniform background, is produced, thereby enabling easy extraction of particles during image processing.

The liquid to be tested is first photographed at a high magnification, and then at a low magnification, so that diametrically larger columns, not adaptable for easy dying, are dyed as much as possible, and then they are photographed. Thus, the time required for the dyeing process is reduced, and the processing time per test sample is shortened.

When the thickness of the test liquid flow is changed, only the supply of the liquid to be tested is changed, so that it is easy to control its thickness.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A process for [classifying and counting] *analyzing* ingredients of a liquid to be tested, comprising:

flowing said liquid to be tested in a flattened path;

surrounding said liquid to be tested in said flattened path with a sheath liquid;

impinging a light on said flattened path;

photographing said flattened path at a first magnification;

photographing said flattened path at a second magnification; and changing a thickness of said liquid to be tested in said flattened path when photographing at said first and second magnifications, whereby said thickness remains less than a depth of field of a lens used in said photographing.

2. A process according to claim 1, wherein the step of changing a thickness includes changing a flow rate of at least one of said liquid to be tested and said sheath liquid.

3. A process according to claim 1, further comprising:

adjusting an amount of said light according to said first and second magnifications.

4. A process according to claim 1, further comprising diffusing said liquid during photographing at one of said first and second magnifications, and not at the other thereof.

5. A process according to claim 4, wherein the one of said first and second magnifications is a lower magnification.

6. A process according to claim 1, further comprising:

simultaneously adjusting an intensity of said light, said thickness, and said magnification to attain a sharp image of particles in said liquid to be tested.

7. A cell analyzing system comprising:

a strobe for emitting flashes of a light;

at least one lens; said at least one lens being effective for transforming said light into a parallel light;

an iris receiving said parallel light;

adjustable means for adjusting an opening of said iris;

a condenser lens receiving light from said iris;

a flow cell;

a reduced flow passage in said flow cell;

said reduced flow passage including a thickness which narrows gradually in a downstream direction;

a flattened flow passage;

said flattened flow passage communicating with a downstream side of said reduced flow passage;

a nozzle having an end facing in a downward direction toward an upstream side of said reduced flow passage;

a test liquid supply means;

said test liquid supply means being connected to said nozzle;

said test liquid supply means including means for changing a supply quantity of said liquid to be tested;

a sheath liquid supply means connected to an upstream side of said reduced flow passage;

at least said flattened flow passage being transparent;

said light from said condenser lens passing through said flattened flow passage, including liquids therein;

an objective lens disposed behind said flow cell;

at least first and second projection lenses;

said at least first and second projection lenses having first and second different magnifications;

means for selectably disposing said first and second projection lenses in a path of light from said flattened flow path;

means for photographing an image from a selected one of said first and second projection lenses; and means for controlling a flow such that a thickness of said test liquid differs for different magnifications.

8. A system according to claim 7, wherein said means for selectably disposing includes means for changing a path length of said light, whereby a sharp focus is maintained at said first and second magnifications.

9. A system according to claim 7, [further comprising] *wherein said means for controlling a flow includes* means for changing a thickness of said test liquid in said flattened flow passage.

10. A system according to claim 9 wherein said means for changing a thickness includes changing a flow of at least one of said test liquid and said sheath liquid.

11. A system according to claim 7, further comprising means for diffusing said light from said strobe during at least a lower of said first and second magnifications.

12. A system according to claim 7, wherein the means for diffusing includes means for diffusing said light only during said lower of said first and second magnifications.

13. A method for photographing a test liquid comprising:

flowing said test liquid through a reduced flow passage;

flowing a sheath liquid through said reduced flow passage;

flowing said test liquid and said sheath liquid from said reduced flow passage through a flattened flow passage;

passing a parallel light through said flattened flow passage;

forming an image of said parallel light passing through said flattened flow passage;

controlling a thickness of said test liquid in said flattened flow passage to a value permitting said image to be sharp;

the step of controlling including changing a flow relationship of said test liquid and said sheath liquid;

changing a magnification of said image; and changing a thickness of said test liquid in said flattened flow passage to a value within a depth of field of an apparatus forming said image.

14. A method for photographing a test liquid comprising:

flowing said test liquid through a reduced flow passage;

flowing a sheath liquid through said reduced flow passage;

flowing said test liquid and said sheath liquid from said reduced flow passage through a flattened flow passage;

passing a parallel light through said flattened flow passage;

forming an image of said parallel light passing through said flattened flow passage;

controlling a thickness of said test liquid in said flattened flow passage to a value permitting said image to be sharp; [and]

the step of controlling including changing a flow relationship of said test liquid and said sheath liquid;

forming a first image at a first magnification;

controlling said thickness to a first value within a depth of field at said first magnification;

forming a second image at a second magnification; and controlling said thickness to a second value within a depth of field at said second magnification.

*15. A cell analyzing system comprising:*

*a light source for emitting flashes of a light;*

*a condenser lens receiving light from said light source;*

*a flow cell;*

*a reduced flow passage in said flow cell;*

*said reduced flow passage including a thickness which narrows gradually in a downstream direction;*

*a flattened flow passage;*

*said flattened flow passage communicating with a downstream side of said reduced flow passage;*

*a nozzle having an end facing in a downward direction toward an upstream side of said reduced flow passage;*

*a test liquid supply means;*

*said test liquid supply means being connected to said nozzle;*

*said test liquid supply means including means for changing a supply quantity of said liquid to be tested;*

*a sheath liquid supply means connected to an upstream side of said reduced flow passage;*

*at least said flattened flow passage being transparent;*

*said light from said condenser lens passing through said flattened flow passage, including liquids therein;*

*an objective lens disposed behind said flow cell;*

*at least first and second projection lenses;*

*said at least first and second projection lenses having first and second different magnifications;*

*means for selectably disposing said first and second projection lenses in a path of light from said flattened flow path;*

*means for photographing an image from a selected one of said first and second projection lenses; and*

*means for controlling a flow such that a thickness of said test liquid differs for different magnifications.*

*16. A cell analyzing system comprising:*

*a light source for emitting flashes of a light;*

*adjustable means for adjusting an amount of light;*

*a condenser lens receiving light from said light source;*

*a flow cell;*

*a reduced flow passage in said flow cell;*

*said reduced flow passage including a thickness which narrows gradually in a downstream direction;*

*a flattened flow passage;*

*said flattened flow passage communicating with a downstream side of said reduced flow passage;*

*a nozzle having an end facing in a downward direction toward an upstream side of said reduced flow passage;*

*a test liquid supply means;*

*said test liquid supply means being connected to said nozzle;*

*said test liquid supply means including means for changing a supply quantity of said liquid to be tested;*

*a sheath liquid supply means connected to an upstream side of said reduced flow passage;*

*at least said flattened flow passage being transparent;*

*said light from said condenser lens passing through said flattened flow passage, including liquids therein;*

*an objective lens disposed behind said flow cell;*

*at least first and second projection lenses;*

*said at least first and second projection lenses having first and second different magnifications;*

*means for selectably disposing said first and second projection lenses in a path of light from said flattened flow path;*

*means for photographing an image from a selected one of said first and second projection lenses; and*

*means for controlling a flow and an amount of light such that a thickness of said test liquid and the amount of light in the flattened flow passage differs for different magnifications.*

* * * * *